United States Patent [19]
Tann et al.

[11] Patent Number: 5,283,359
[45] Date of Patent: Feb. 1, 1994

[54] PROCESS FOR PREPARING ALBUTEROL, ACETAL, HEMI-ACETAL, AND HYDRATES OF ARYLGLYOXAL INTERMEDIATES THEREOF

[75] Inventors: Chou-Hong Tann, Berkeley Heights; T. K. Thiruvengadam, Edison; John Chiu, Parsippany; Michael Green, Paterson; Timothy L. McAllister, Fords; Cesar Colon, Rahway; Junning Lee, Springfield, all of N.J.

[73] Assignee: Schering Corp., Kenilworth, N.J.

[21] Appl. No.: 30,185

[22] PCT Filed: Sep. 6, 1991

[86] PCT No.: PCT/US91/06248
§ 371 Date: Mar. 1, 1993
§ 102(e) Date: Mar. 1, 1993

[87] PCT Pub. No.: WO92/04314
PCT Pub. Date: Mar. 19, 1992

[51] Int. Cl.$^5$ .............. C07C 69/76; C07F 5/02
[52] U.S. Cl. .................. 560/53; 549/372; 549/350; 562/463; 564/177; 564/169; 564/355; 564/363; 568/6
[58] Field of Search .......... 560/53; 562/463; 549/350, 372; 564/169, 177, 355, 363; 568/6

[56] References Cited
PUBLICATIONS
Collin, D. T. et al J. Med. Chem. 13(4) 674–80 1970.

*Primary Examiner*—Paul J. Killos
*Attorney, Agent, or Firm*—Joseph T. Majka; Edward H. Mazer; Eric S. Dicker

[57] ABSTRACT

The preparation of arylethanolamines, and in particular albuterol (salbutamol), together with their novel boron, acetal and hemi-acetal intermediates is described.

14 Claims, No Drawings

PROCESS FOR PREPARING ALBUTEROL, ACETAL, HEMI-ACETAL, AND HYDRATES OF ARYLGLYOXAL INTERMEDIATES THEREOF

FIELD OF THE INVENTION

The present invention relates to the preparation of arylethanolamines, and in particular to the synthesis of albuterol (salbutamol) and other arylethanolamines of the type disclosed in British Patent Specifications Nos. 1,200,886, 1,214,012 and 1,266,058. Furthermore, the present invention also relates to the preparation of certain novel boron-complexes and of certain acetals, hemi-acetals and hydrates of arylglyoxals useful as intermediates in preparing said arylethanolamines, particularly albuterol.

BACKGROUND

British Patent Specification No. 1,200,886 discloses certain arylethanolamines, which are theraputically active compounds useful as antihypertensive and bronchodilating agents, and two methods for their preparation.

British Patent Specification 1,200,886, "Pharmazeutische Wirkstoffe (Synthesen, Patente, Anwendungen)", Vol. 5, by Kleeman and Engel (2nd Edition, New York and Stuttgart), p. 813, 1982 and "Pharmaceutical Manufacturing Encyclopedia", Second Edition, Vol. 1, by Marshall Sittig, Noyes Publications, Park Ridge, N.J., U.S.A., 1988, pp. 31-33, teach the preparation of albuterol by condensation of a haloacetophenone with a benzyl protected t-butyl amine. These processes have the disadvantage of producing albuterol in low yields with a significant generation of waste or undesirable by-products. Part of this inefficiency is due to the requisite use of multiple reducing agents, i.e. lithium aluminum hydride, sodium borohydride and hydrogenation with palladium/carbon catalysts, accompanied by multiple clean-up procedures. Another reason for the inefficiency is the requisite use of a benzyl-protecting group on the amine to prevent dialkylation of the amine, necessitating further deprotection and clean-up procedures.

British Patent Specification 1,247,370 teaches the preparation of albuterol by condensation of t-butylamine with arylglyoxal, followed by multiple reductions using lithium aluminum hydride and sodium borohydride. This patent also teaches a process for preparing arylglyoxals requiring multiple steps using low temperatures (e.g. room temperature) and long reaction periods (e.g. up to one week) to minimize undesirable polymerization of the labile arylglyoxal. This process has the disadvantage of producing albuterol in low yields with significant generation of undesirable by-products.

Arylglyoxals are compounds useful as intermediates for preparing pharmaceutical compounds. Conventional processes for preparing arylglyoxal compounds are known in the art. N. Kornblum, J. W. Powers, G. J. Anderson, W. J. Jones, H. O. Larson, O. Levand and W. M. Weaver, JACS, Vol. 79, (1957) page 6562, J. March, Advanced Organic Chemistry, Reactions, Mechanisms, and Structure, Third Edition, John Wiley & Sons, New York, N.Y., (1985) pp. 1081-1083 and British Patent Specification 1247370 teach the oxidation of primary halides and esters of primary alcohols to aldehydes with dimethyl sulfoxide. M. B. Floyd, M. T. Du, P. F. Fabio, L. A. Jacob and Bernard D. Johnson, J. Org. Chem. Vol. 50, (1985), pp. 5022-5027 and R. Desmond, S. Mills, R. P. Volante and I. Shinkai, Synthetic Comm. Vol. 19 (3 and 4), (1989) pp. 379-385 disclose the reaction of acetophenones with aqueous hydrobromic acid (HBr) in DMSO leading to the formation of arylglyoxals. G. Cardillo, M. Orena and S. Sandri, J.C.S. Chem. Comm. (1976) pp. 190 disclose the preparation of aldehydes by reacting alkyl halides with potassium chromate in hexamethylphosphoramide in the presence of crown ethers. K. R. Henery-Logan and T. L. Fridinger, Chemical Communications, (1968) pp. 130-131 disclose the conversion of $\alpha,\alpha$-dichloroacetophenone with sodium methoxide in methyl alcohol to phenylglyoxals. V. E. Gunn and J. P. Anselme, J. Org. Chem., Vol. 42, No. 4, (1977) pp. 754-755 disclose the conversion of phenacylbromides to phenylglyoxals with N,N-diethyl and N,N-dibenzylhydroxylamines. H. A. Riley and A. R. Gray, Organic Synth. Coll. Vol. 2, pp. 509-511 disclose the conversion of acetophenone to phenylglyoxal with selenium dioxide as the oxidant. The above-cited processes have severe limitations. For example, most of these references teach the direct preparation of arylglyoxals, which may be labile or unstable. Also, such processes generally are not adaptable to using a wide range of substrates or precursors to prepare arylglyoxals. In addition, most of the cited processes utilize toxic oxidants such as selenium oxides, chromates and the like which tend to be unsuitable for preparing pharmaceutical compounds.

Moreover, we have found that the use of aqueous hydrogen bromide as a brominating agent was not adaptable for certain aryl substrates since use of the aqueous reagent resulted in undesirable ring bromination.

In view of the problems with processes taught in the prior art, it would clearly be desirable to provide a new process for preparing arylethanolamines such as albuterol in higher yields and with reduced waste or generation of by-products. It would also be desirable to provide new intermediates or derivatives for preparing albuterol which would result in a simplified preparation of this compound. We have surprisingly found that the foregoing objectives may be achieved by utilizing specified precursors for preparing the arylglyoxal hydrates, that is, the acetals and hemi-acetals. These acetals and hemi-acetals, which we have found to be significantly more stable than the arylglyoxal hydrates, may be deprotected under relatively mild conditions to yield the desired hydrates of the arylglyoxal. Furthermore, we have found a single reducing agent which may be used for preparing albuterol, instead of the multiple reducing agents of British 1,247,370 and 1,200,886. It would also be desirable to provide a process which requires fewer reaction and cleanup steps than other processes previously taught. In addition, it would also be desirable to provide an efficient process for preparing the acetal and hemi-acetal derivatives which can serve as substrates or precursors for preparing the desired hydrates of arylglyoxals. By employing such intermediates and processes, it is believed that many of the limitations and problems of the processes described in the above references for making albuterol can be overcome.

SUMMARY OF THE INVENTION

In a first embodiment, the present invention is directed toward the novel boron-arylethanolamine complex represented in its monomeric form as formulas (XIII)-A and -B:

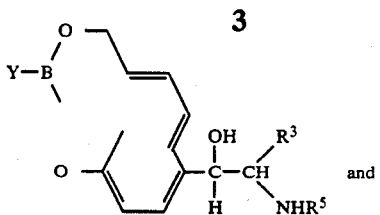

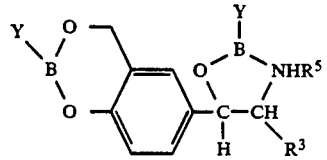

wherein Y is —OR$^{17}$ or —OH, wherein R$^{17}$ is C-1 to C-6 alkyl and R$^3$ and R$^5$ independently represent hydrogen, alkyl, aryl or substituted aryl. Preferably Y is —OCH$_3$, R$^3$ represents hydrogen and R$^5$ represents tertiary-butyl (t-butyl). The boron-arylethanolamine complex (XIII) can serve as a valuable intermediate for preparing arylethanolamines such as albuterol.

In a second embodiment, the present invention is directed towards a process for preparing an arylethanolamine of the formula:

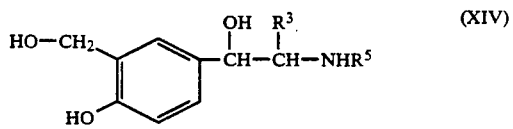

wherein R$^3$ and R$^5$ independently represent hydrogen, alkyl, aryl or substituted aryl, comprising cleaving boron-arylethanolamine complex (XIII)-A and -B of the first embodiment to give the desired arylethanolamine (XIV). Preferably, boron-arylethanolamine complex (XIII)-A and -B is cleaved by addition of an acid and an alcohol to the reaction mixture. Also preferred is that the reaction mixture is distilled to remove any spent boron. Arylethanolamine (XIV) wherein R$^3$ is hydrogen and R$^5$ is t-butyl is known as albuterol.

In a third embodiment, the present invention is directed towards a process for preparing the arylethanolamine of formula (XIV), comprising reducing a Schiff's base of the formula:

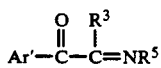

wherein R$^3$ and R$^5$ are as defined in the second embodiment, and Ar' is

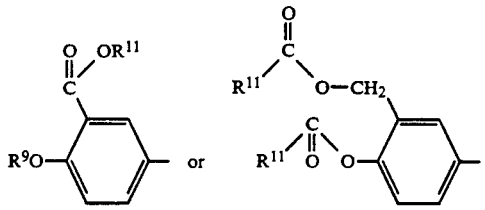

wherein R$^9$ represents hydrogen or acyl, and R$^{11}$ represents hydrogen or alkyl, with a borane-thioether reagent to give arylethanolamine (XIV). Preferably the

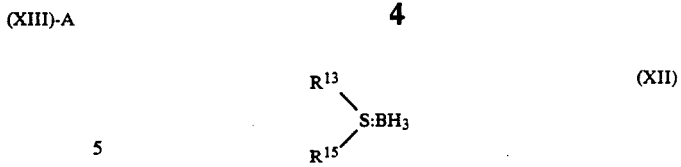

wherein R$^{13}$ and R$^{15}$, which may be the same or different, represent C-1 to C-6 alkyl, or, together with the sulfur atom, represent a ring containing from 3 to 6 carbon atoms and 1 or 2 sulfur or oxygen atoms, or together with the sulfur atom represent a polymeric thiohydrocarbon.

In a fourth embodiment of the present invention, the Schiff's base (XI) of the third embodiment is prepared by contacting a glyoxal hydrate of formula (IX):

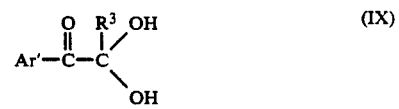

or a hemi-acetal of formula (V):

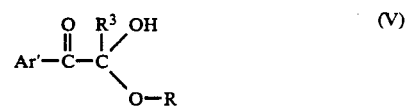

wherein Ar' and R$^3$ are as defined in the third embodiment, and R represents alkyl, substituted alkyl, cycloalkyl, cycloalkylalkyl, hydroxyalkyl, aryl, substituted aryl, arylalkyl, substituted arylalkyl, heterocyclic or heterocyclic alkyl, with an amine of the formula H$_2$NR$^5$ (X), wherein R$^5$ is as defined hereinbefore to give the Schiff's base (XI).

In a fifth embodiment of the present invention, the glyoxal hydrate (IX) of the fourth embodiment is prepared by hydrolyzing an acetal (VII) or hemi-acetal (V) of the formula:

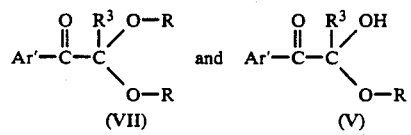

wherein Ar' and R$^3$ are as defined in the second and third embodiments, and R represents alkyl, substituted alkyl, cycloalkyl, cycloalkylalkyl, hydroxyalkyl, aryl, substituted aryl, arylalkyl, substituted arylalkyl, heterocyclic or heterocyclic alkyl to give hydrate (IX).

In a sixth embodiment of the present invention, the acetal (VII) or hemi-acetal (V) of the fifth embodiment is prepared by contacting a compound of formula (II):

wherein Ar' and R$^3$ are as defined in the second or third embodiment, and L is a leaving group such as bromo, chloro, iodo, mesylate, triflate, brosylate or tosylate, with a sulfoxide and an alcohol of the formula ROH, wherein R is as defined in the fourth embodiment, or

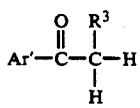

(I)

wherein Ar' and $R^3$ are as defined in the second or third embodiment, with a halogenating agent, a sulfoxide, and an alcohol of formula ROH, to give the acetal or hemi-acetal of formula (VII) or (V).

In a seventh embodiment, the present invention is directed toward a process for preparing acetals and hemi-acetals of the formula:

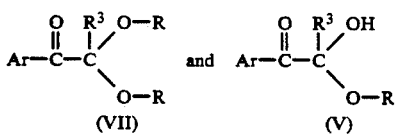

(VII)    (V)

wherein

Ar represents aryl or substituted aryl;

R represents alkyl, substituted alkyl, cycloalkyl, cycloalkylalkyl, hydroxyalkyl, aryl, substituted aryl; arylalkyl, substituted arylalkyl, heterocyclic or heterocyclic alkyl and $R^3$ represent hydrogen, alkyl, aryl or substituted aryl, comprising contacting a compound of formula (II):

(II)

wherein Ar and $R^3$ are as defined hereinbefore, and L is a leaving group such as bromo, chloro, iodo, mesylate, triflate, brosylate or tosylate, with a sulfoxide and an alcohol of the formula ROH, wherein R is as defined above, or alternatively, contacting a compound of formula (I):

(I)

wherein Ar and $R^3$ are as defined hereinbefore, with a halogenating agent, a sulfoxide, and an alcohol of formula ROH, to give the acetal or hemi-acetal of formula (VII) or (V).

In an eighth embodiment, the present invention is directed toward a process for preparing glyoxal hydrates of formula (IX):

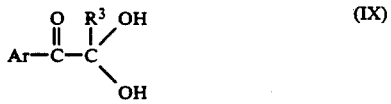

(IX)

wherein Ar and $R^3$ are as defined in the seventh embodiment, comprising hydrolyzing acetal (VII) or hemiacetal (V) as prepared in the seventh embodiment to give hydrate (IX).

In a ninth embodiment, the present invention is directed to acetals and hemi-acetals of the formula:

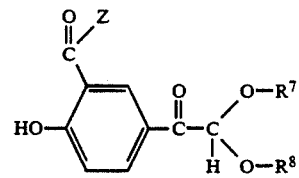

(XX)

wherein Z is $-NH_2$, $-OH$ or $-OR^6$, such that $R^6$ represents hydrogen or alkyl of one to ten carbon atoms, and $R^7$ and $R^8$ independently represent hydrogen, alkyl, substituted alkyl, cycloalkyl, cycloalkylalkyl, hydroxyalkyl, aryl, arylalkyl, substituted arylalkyl, heterocyclic or heterocyclic alkyl with the proviso that only one of $R^7$ or $R^8$ is hydrogen, or $R^7$ and $R^8$ together with the oxygen atoms forms a five or six membered ring. Preferably, $R^7$ and $R^8$ represent hydrogen or alkyl of one to ten carbon atoms with the proviso that only one of $R^7$ or $R^8$ is alkyl, preferably of one to four carbon atoms. Most preferably, Z is $-OCH_3$ and $R^7$ and $R^8$ independently represent methyl, isopropyl or n-butyl.

The present invention has the advantage of enabling preparation of certain arylethanolamines such as albuterol via acetals, hemi-acetals and arylglyoxal hydrate intermediates more efficiently and economically, i.e. in higher yields and purity, with less by-product generation and in less time, compared with other known processes. The present invention has the advantage of providing novel intermediates such as the boron-arylethanolamine complex (XIII), acetals and hemi-acetals (XX) which are useful in simplifying the preparation of albuterol. In one embodiment, the present invention has the advantage of providing a process which may utilize a single reducing agent capable of reducing three different groups on the same molecule. In another embodiment, the present process for preparing arylglyoxal hydrates has the advantage of being adaptable to using a wide range of substrates for its preparation. The present invention has the further advantage of allowing the preparation of arylglyoxal hydrates, acetals and hemi-acetals at temperatures greater than ambient with little or no by-product formation resulting from undesirable polymerization of labile arylglyoxals. Where a brominating agent is used, the present process can employ anhydrous hydrogen bromide or bromine to maintain the advantage of minimizing or eliminating undesirable ring bromination. And still yet a further advantage is that it requires even fewer reaction or cleanup procedures than other processes previously taught.

DETAILED DESCRIPTION OF THE INVENTION

When utilized herein the terms listed hereinbelow, unless otherwise indicated, are defined as follows:

alkyl—represents a straight chain saturated hydrocarbon moiety having from 1 to 10 carbon atoms, preferably from 1 to 6 carbon atoms or a branched hydrocarbon moiety of 3 to 10 carbon atoms, preferably from 3 to 6 carbon atoms, such as for example methyl, ethyl, propyl, isopropyl, n-butyl, isobutyl, pentyl, hexyl, decyl and the like; the term "substituted alkyl" refers to an alkyl moiety in which one or more of the hydrogen atoms can be substituted with halo, hydroxyl, aryl or cycloalkyl;

cycloalkyl—represents a saturated hydrocarbon ring having from 3 to 10 carbon atoms, preferably from 3 to 6 carbon atoms, such as for example cyclopropyl, cyclobutyl, cyclopentyl, cyclohexyl and the like;

acyl—represents the moiety —CO—J wherein J represents alkyl, cycloalkyl or aryl.

aryl—represents a carbocyclic moiety containing at least one benzenoid-type ring, with the aryl moiety having from 6 to 14 carbon atoms, for example phenyl, naphthyl, indenyl, indanyl and the like; the term "substituted aryl" refers to an aryl moiety substituted with one to three substituents independently selected from aryl, alkyl, alkoxy, halo, trihalomethyl, cyano, nitro, —CONH$_2$, hydroxy, protected hydroxy, hydroxyalkyl, protected hydroxyalkyl, mercapto or carboxy and salts or esters thereof, arylalkyl or substituted arylalkyl—refers to a an aryl or substituted aryl moiety bonded to an adjacent structural element through an alkyl moiety, such as for example phenylmethyl, 2-chlorophenylethyl and the like;

heterocyclic—represents a cyclic group having at least one O, S and/or N interrupting a carbocyclic ring structure and having a sufficient number of delocalized pi ($\pi$) electrons to provide aromatic character, with the aromatic heterocyclic group having from 2 to 14, preferably from 2 to 6 carbon atoms, for example 2-, 3- or 4-pyridyl, 2- or 3-furyl, 2- or 3-thienyl, 2-, 4- or 5-thiazolyl, 1-, 2-, 4- or 5-imidazolyl, 2-, 4- or 5-pyrimidinyl, 2-pyrazinyl, 3- or 4-pyridazinyl, 3-, 5- or 6-(1,2,4-triazinyl), 3- or 5-(1,2,4-thiadizolyl), 2-, 3-, 4-, 5-, 6- or 7 -benzofuranyl, 1-, 2-, 3-, 4-, 5-, 6- or 7-indolyl, 1-, 3-, 4- or 5-pyrazolyl, 2-, 4- or 5-oxazolyl and the like;

heterocyclic alkyl—represents a heterocyclic moiety bonded to an adjacent structural element through an alkyl moiety;

hydroxyalkyl—represents an alkyl moiety as defined hereinbefore wherein one of the hydrogen atoms is replaced with a hydroxy moiety, such as hydroxymethyl, 2-hydroxyethyl and the like;

protected hydroxy or protected hydroxyalkyl—represents a hydroxy group or a hydroxyalkyl group as defined hereinbefore wherein the hydroxy group is protected from reaction by converting the hydroxy to a protected moiety such as —OCH$_3$, —OCH$_2$phenyl, —OCOCH$_3$, —OSi(CH$_3$)$_3$, —OSi(CH$_3$)$_2$(t-Butyl),

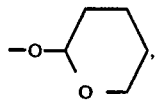

and the like. Of course other protecting groups well known in the art may be used. After the reaction or reactions, the protecting groups may be removed by standard procedures known in the art, such as hydrolysis with mineral acids such as hydrochloric acid;

halo—represents fluoro, chloro, bromo or iodo;

trihalomethyl—represents trichloromethyl and trifluoromethyl;

alkoxy—represents an alkyl moiety as defined above covalently bonded through an oxygen atom, as for example, methoxy, ethoxy, propoxy, pentyloxy, hexyloxy, decyloxy and the like;

carboxy—represents the moiety —COOH; and mercapto—represents the moiety —SR$^1$ wherein R$^1$ represents alkyl or aryl;

polymeric thiohydrocarbon—represents a polymer containing atoms of sulfur, hydrogen and carbon; the sulfur atoms are present in the polymeric thiohydrocarbon in a thioether configuration, i.e. a —C—S—C— configuration.

A description of the processes and intermediates associated with the present invention are schematically illustrated by the following reaction scheme in which which Ar, Ar', R3 and R5 are as defined for formulas (XIV), (XI), (V) and (VII) above, Hal is halo and L is a leaving group:

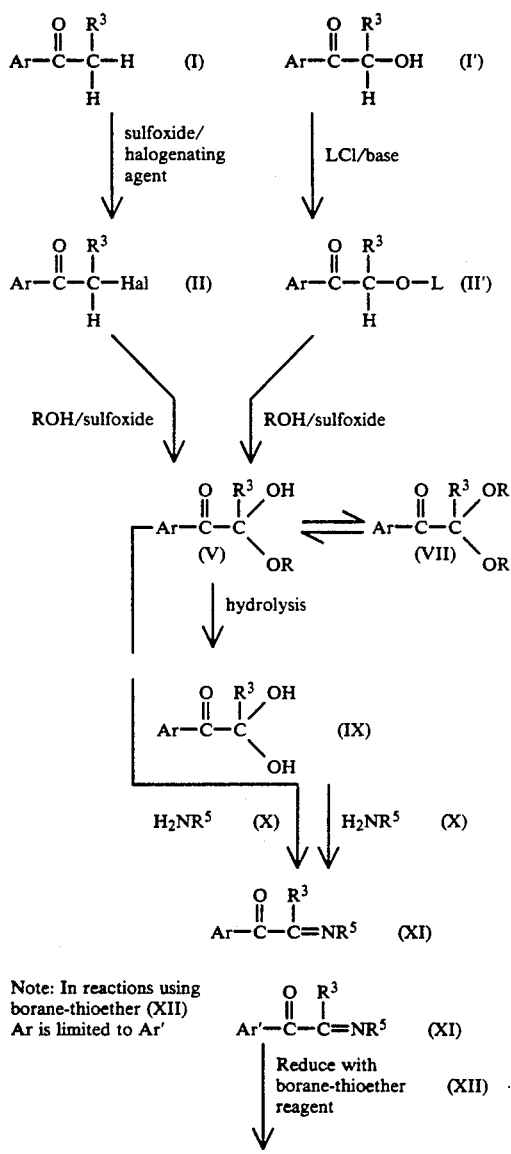

Note: In reactions using borane-thioether (XII) Ar is limited to Ar'

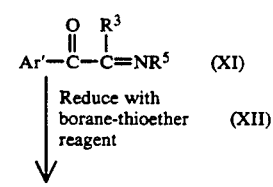

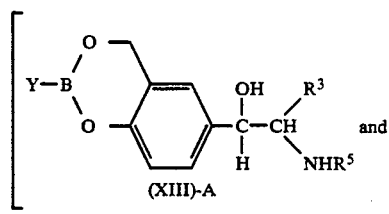

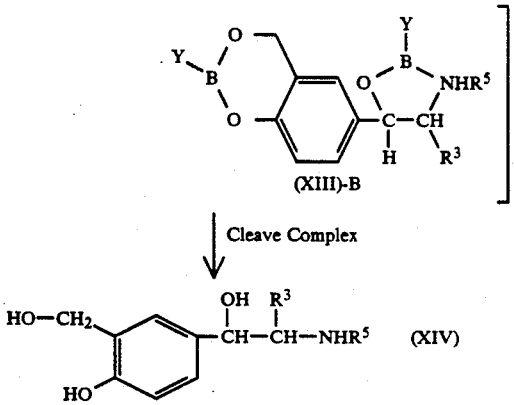

(XIII)-B

↓ Cleave Complex $$\text{HO-CH}_2\text{-}\underset{\text{HO}}{\bigcirc}\text{-CH-CH-NHR}^5 \quad (XIV)$$
$$\phantom{HO-CH_2-}\overset{OH}{|}\phantom{-}\overset{R^3}{|}$$

The compound of formula (II) wherein Hal represents halo such as chloro, bromo or iodo, and $R^3$ represents hydrogen, alkyl or aryl, can be prepared by contacting the compound of formula (I) with a halogenating agent and a sulfoxide such as DMSO. The halogenating agent employed can be from a broad class of compounds which will incorporate one of the halogen elements, preferably chlorine or bromine, into compound (I). Such halogenating agents include but are not limited to bromine ($Br_2$), iodine ($I_2$), chlorine ($Cl_2$), hydrogen bromide (HBr) and hydrogen chloride (HCl). The halogenating agent can be used in amounts ranging from about two moles to about catalytic amounts per mole of compound (I), preferably from about 0.8 to about 0.4 mole halogenating agent. Also preferred is that the halogenation is carried out under anhydrous or substantially anhydrous conditions. Methods for utilizing such reagents are known, as described in J. March, Advanced Organic Chemistry, Reactions, Mechanisms and Structure, Third Edition, John Wiley and Sons, New York, (1985), 1346 pp. The sulfoxide employed can be alkyl sulfoxides wherein each alkyl substituent has one to four carbon atoms, such as dimethylsulfoxide (i.e. $CH_3SOCH_3$ or DMSO), diethylsulfoxide, dipropylsulfoxide and dibutylsulfoxide, most preferably DMSO. The sulfoxide can be employed in amounts ranging from excess to about two:one mole compound (I) [moles sulfoxide:mole compound (I)], preferably from about 20 to 4, more preferably from about 10 to 6 moles, most preferably about 6 moles sulfoxide. The compounds of formula (II') can be prepared by contacting compound (I') with an acid chloride of the formula LCl wherein L is a leaving group represented by tosyl, triflyl, brosyl, mesyl and the like, in the presence of a base, as described in J. March, pp. 444 and 628 supra.

Acetals (VII) and hemi-acetals (V) can be prepared by contacting compounds (II) or (II') with a sulfoxide and an alcohol of the formula ROH, wherein R is alkyl, cycloalkyl, hydroxyalkyl or aryl as defined hereinbefore. The sulfoxide used to prepare acetals (VII) and hemi-acetals (V) can be employed in amounts similar to that described for preparing compound (II), above. The alcohol employed in the preparation of the acetals (VII) and hemiacetals (V) can be from a broad class of hydroxyl containing organic compounds, as defined in the Condensed Chemical Dictionary, 10th Edition, revised by Gessner G. Hawley, Van Nostrand Reinhold Company, New York, 1981. The alcohol can be monohydric (one OH group) or dihydric (two OH groups-diols). Representative monohydric alcohols include methanol (i.e. $CH_3OH$), ethanol, propanol, iso-propanol, n-butanol, n-hexanol, 4-methyl-2-pentanol and the like. Monohydric alcohols also include the class of C-3 to C-8 cyclic alcohols such as cyclohexanol, cycloheptanol and the like; the class of C-6 to C-15 aryl alcohols such as phenol, benzyl alcohol, 1-naphthol and the like; and the class of heterocyclic alcohols such as 2-hydroxy pyridine, furfuryl alcohol and the like. The diols can include C-2 to C-10 glycols, such as ethylene glycol, propylene glycol, 1,2-butanediol, 1,4-butanediol, pentanediols and the like. Where suitable mixtures of any of the alcohols can be employed, such as a mixture of two or more monohydric alcohols or a mixture of a monohydric alcohol and a dihydric alcohol. The alcohol can be employed in amounts ranging from an excess to about 2:1 (moles alcohol:mole compound (II)), preferably from about 30 to 10, more preferably from about 20 to 15 moles alcohol. In general, the use of higher amounts of alcohol tends to favor formation of the acetals (VII) over the hemi-acetals (V).

Generally the reactants are stirred during the reaction. The reactants can be contacted for a time sufficient to effect the desired completion of the reaction, as evidenced by disappearance of the starting materials. Such times will depend upon the temperatures and amount of reagent employed, and can range from about fifteen minutes to about 24 hours or more, preferably about one hour.

Acetals (VII) and hemi-acetals (V) can be recovered by conventional procedures such as solvent extraction, filtration, phase separation, crystallization or the like. Typically, the reaction mixture is added to ice water and the precipitate is filtered out to give the desired acetals (V) and hemi-acetals (VII).

The arylglyoxal hydrate (IX) can be prepared by conventional hydrolysis of the acetals (VII) and hemi-acetals (V) in the reaction mixture with mineral or organic acids such as hydrochloric, sulfuric or acetic acid. The amount of acid can range from excess to about 0.1 moles of acid per mole of acetal (VII) or hemi-acetal (V), preferably from about 10 to about 0.5 moles acid per mole of acetal (VII) or hemi-acetal (V). Similarly, the acid can be contacted with any isolated or recovered acetal (VII) or hemi-acetal (V) to give arylglyoxal hydrate (IX). In situations where the reaction mixture containing the acetals (VII) and hemi-acetals (V) already has sufficient acid for hydrolysis, further addition of acid to the reaction mixture may be unnecessary.

Arylglyoxal hydrate (IX) can be converted to its corresponding arylglyoxal (IX')' with the removal of water, as illustrated in the proposed equilibrium:

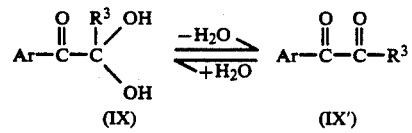

In the above illustration, preferably $R^3$ is hydrogen.

The present process is carried out preferably without using any solvents other than excess amounts of the reactants themselves. Where an additional solvent is employed, however, such solvents can include aromatic hydrocarbons such as xylene, benzene, toluene and the like, or an alkane solvent of 6 to 10 carbon atoms. Where additional solvent is employed, the solvent can be used in amounts ranging from excess compared with any of the reactants to an amount sufficient to at least partially solubilize one or more of the reactants and/or the desired product. It should be noted that the conversion of compound (I) to glyoxal hydrate (IX) can be advantageously carried out in a single pot or reaction vessel in high yield, as demonstrated in Example 1, infra.

The Schiff's base (XI) can be prepared by condensation of either hemi-acetal (V) or arylglyoxal hydrate (IX) with a primary amine $H_2NR^5$ of the formula (X) wherein $R^5$ is defined hereinbefore, preferably in an equimolar ratio or with an excess of the less expensive reactant, which is normally the amine. The condensation can be carried out in the presence of a suitable solvent, including C-1 to C-6 alkanols such as methanol, ethanol, hexanol and the like; aromatic hydrocarbons such as those described previously; C-5 to C-10 aliphatic hydrocarbons; ethers such as diethylether, ethylene glycol dimethyl ether (DME) or dioxane; tetrahydrofuran (THF); or mixtures of any of the above thereof can be used. Alternatively, the condensation can be carried out neat, in which an excess of amine (X) is employed. Most preferably, DME or toluene is used. Generally, the organic solvent used to prepare Schiff's base (XI) should also serve as solvent in the next stage, i.e., reduction with the borane-thioether reagent (XII), since the reduction can be carried out more economically in a single-pot reaction following the condensation. The condensation can be carried out at temperatures which can range from about 0° C. to the reflux temperature of the solvent, preferably at about ambient temperature.

The novel boron-arylethanolamine complex (XIII) can be prepared by reducing the Schiff's base (XI) with borane-thioether reagent (XII), followed by treatment with an alcohol and an acid. The borane-thioether reagent can be of the formula:

(XII)

wherein $R^{13}$ and $R^{15}$ may be the same or different, and can represent C-1 to C-6 alkyl, or together with the sulfur atom can represent a heterocyclic ring which contains from 3 to 6 carbon atoms and may contain 1 or 2 sulfur or oxygen atoms, or together with the sulfur atom can represent a polymeric thiohydrocarbon. Preferably $R^{13}$ and $R^{15}$ are C-1 to C-6 alkyl, more preferably ethyl, most preferably methyl. The borane-thioether reagent wherein $R^{13}$ and $R^{15}$ are methyl is known as borane-dimethylsulfide (BMS), a commercially available liquid. Also preferred is that $R^{13}$ and $R^{15}$, together with the sulfur atom, represents a polymeric thiohydrocarbon as taught in U.S. Pat. Nos. 4,029,706 and 3,928,293. These patents describe the preparation and use of borane thiopolymer complexes, i.e. complexes of boron trihydride ($BH_3$) with solid particulate insoluble cross-linked thiohydrocarbon polymers, which may be more particularly characterized as solid, particulate, insoluble, cross-linked aliphatic, cycloaliphatic or aromatic thiohydrocarbon polymers containing a substantial plurality of sulfur atoms; said sulfur atoms being in a thioether configuration. The polymeric borane thiopolymer complexes are characterized in that a major proportion of the sulfur atoms in the thiohydrocarbon polymers (at least 80%) are in complex combination with $BH_3$ molecules. The borane thiopolymer complexes are stable at room temperature. This stability, and the property that such complexes are solids, makes them easy to use and recover (i.e. via filtration). The borane thiopolymer complexes can be prepared by contacting diborane gas with a selected polyether, as described in U.S. Pat. Nos. 4,029,706 and 3,928,293, whose preparative teachings are incorporated herein by reference. The borane thiopolymer complexes have the advantage of substantially reducing the sulfur-containing odors that otherwise result from reaction of the Schiff's base with non-polymeric borane-thioether reagents. Also, spent borane thiopolymer reagents can advantageously be separated from the reaction mixture by convenient recovery procedures, such as by filtration.

Preferably, a borane-thioether reagent (XII) is chosen to allow ready removal of spent boron and of the organic sulfide reactants. For example, spent dimethyl sulfide can be removed by distillation and spent boron can be removed from the reaction mixture by distillation as trimethylborate after addition of methanol and acetic acid. Preferably anhydrous aprotic solvents are employed, such as toluene, DME, THF, dioxane, xylenes and the like. The borane-thioether reagent (XII) can be employed in amounts ranging from excess to about 1.7 moles [moles borane-thioether reagent (XII):mole Schiff's base (XI)], preferably from about 5 to 2, more preferably from about 3 to 2 moles, most preferably about two moles borane-thioether reagent (XII). The temperature for the reduction can range from ambient to the reflux temperature of the solvent, e.g., at 84° C. in DME, for a time sufficient for the desired completion of the reaction, e.g. 2 to 12 hours or more. Following the reaction between the Schiff's base (XI) and borane-thioether reagent (XII), the boron-arylethanolamine complex is believed to be a polymerized form, as illustrated below:

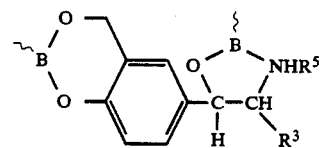

wherein the wavy lines (~~~~~) indicate that the boron-arylethanolamine complexes can be polymerized with other boron-arylethanolamine complexes through a boron atom. These polymerized complexes can be broken down into the more discrete monomers, i.e. boron-arylethanolamine complex (XIII)-A or -B, by an convenient manner, such as by contacting the reaction mixture containing the polymerized complexes with a suitable C-1 to C-6 alcohol. The boron-arylethanolamine complex (XIII)-A or -B monomers can be cleaved to arylethanolamine (XIV) by the addition of acid to the reaction mixture, preferably in the presence of an alcohol. The acid employed can be any one of a number of weak organic acids such as acetic acid, propionic, or butanoic acid, preferably acetic acid. Preferably the alcohol is a C-1 to C-6 alcohol, most preferably methanol. The amount of acid can range from excess to about 4 equivalents [equivalents acid: one equivalent boron-arylethanolamine complex (XIII)], more preferably from about 10 to about 4 equivalents of acid. The amount of alcohol can range from an excess to about 10 equivalents [equivalents alcohol: one equivalent boron-arylethanolamine complex (XIII)], preferably about 1000 to about 100 equivalents alcohol.

Generally, boron-arylethanolamine complex (XIII) will exist in the reaction media as a transient intermediate, as indicated by the bracketing of the complex structures. The boron-arylethanolamine complex (XIII) wherein Y is —OH can be recovered in any convenient manner, such as by addition of water to the reaction mixture, followed by extraction with a water-immiscible solvent such as ethyl acetate. The boron-arylethanolamine complex (XIII) wherein Y is —OR$^6$ can be recovered by addition of a corresponding alcohol of the formula HOR$^6$, wherein R$^6$ is as defined hereinbefore, to the reaction mixture, followed by removal of excess solvent.

After addition of the alcohol and the acid, spent boron e.g. trimethylborate, is distilled out of the reaction mixture, leaving behind the desired arylethanolamine (XIV). The distillation temperature can range from about 20° C. to about 50° C. under vacuum, preferably from about 35° C. to about 40° C. for a time sufficient for desired completion of the reaction, e.g. about two to about 12 hours or more.

The desired arylethanolamine (XIV) can be recovered from the reaction mixture using conventional procedures such as solvent extraction, filtration, phase separation, distillation, crystallization and the like. Preferably, dilute sulfuric acid is added the reaction mixture containing arylethanolamine (XIV), along with a water-miscible organic solvent, such as 2-propanol. The arylethanolamine (XIV) precipitates as the sulfate, e.g. albuterol sulfate, and is removed from the reaction mixture by filtration.

It should be noted that the conversion of 5-glyoxyloyl-salicylic acid methyl ester hydrate to albuterol sulfate can be advantageously carried out in a single pot or reaction vessel in high yield, as demonstrated in Example 7, infra.

The following Examples illustrate the present invention and the manner in which it can be practised, but should not be construed as limitations upon the overall scope of the same.

EXAMPLE 1

5-(Dihydroxyacetyl)-2-hydroxybenzamide (10)

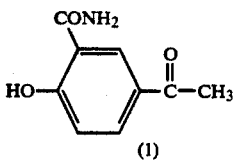

HBr (gas)/DMSO
isopropyl alcohol/heat    Step (a)

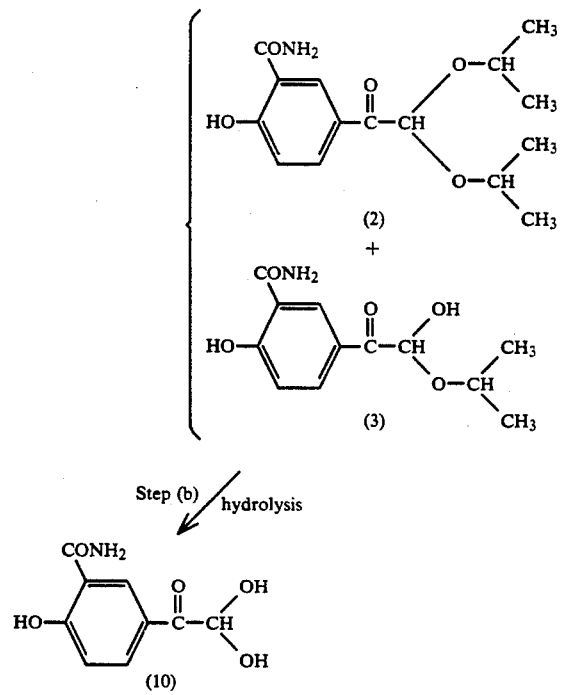

In step (a), 6.23 grams (g) (0.077 mole) of hydrogen bromide gas is bubbled into 180 ml of sieve-dried isopropanol in a 500 ml round bottom flask. To this solution 12.5 g of 5-acetyl-2-hydroxybenzamide (1) (MW 179.17, 0.0698 mole) and 29.3 ml of DMSO (32.3 g, 0.413 mole) are added. The suspension is heated to about 85° C. with adequate agitation to achieve a gentle distillation. The lost isopropanol is replaced throughout the reaction. The progress of the reaction is monitored by both H$^1$-Nuclear Magnetic Spectroscopy (NMR) and high pressure liquid chromatography (HPLC). The reaction is complete within three hours to give a reaction mixture containing 70% of 5-[bis(1-methylethoxy)acetyl]-2-hydroxybenzamide (2) and 2-hydroxy-5-[hydroxy(1-methylethoxy)acetyl]benzamide (3). In step (b), a solution of 1.8 g concentrated sulfuric acid in 100 ml water is added to the reaction mixture. At the same time, the mixture is heated to distill off isopropanol. When 90 percent (%) of the isopropanol is distilled off, another 100 ml of water is added and the mixture is cooled to 50° C. The remainder of isopropanol is distilled off under reduced pressure (300 millimeters mercury(Hg)). The mixture is cooled to ambient temperature with stirring for crystallization to occur. The off-white crystals are filtered, washed thoroughly with water and dried in a draft oven at a temperature of about 60° C. for 16 hours to yield 12.2 g of title compound (10) (83% yield).

EXAMPLE 2

5-(Dihydroxyacetyl)-2-hydroxybenzamide (10)

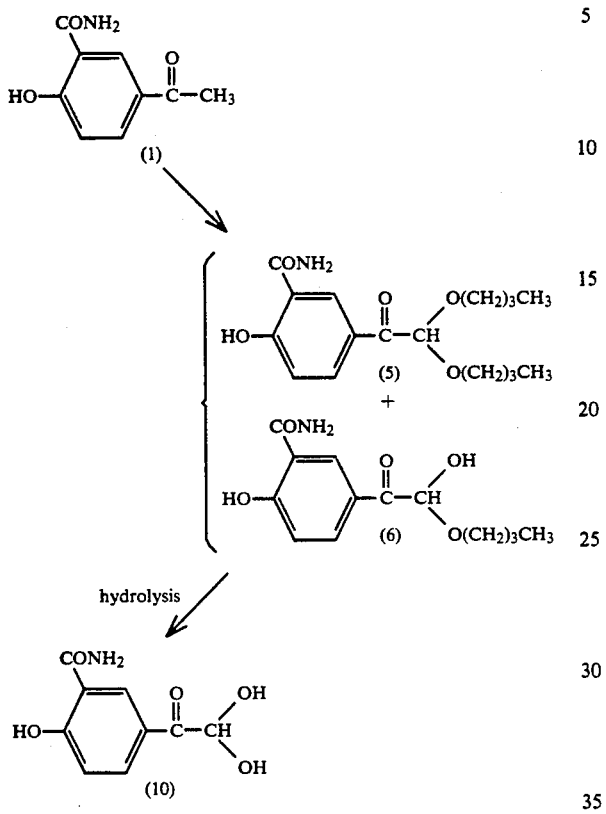

A 250 ml three-necked round bottom flask is equipped with a short-path condenser, addition funnel and thermometer. To the flask under a nitrogen atmosphere is charged 12.5 g (0.07 mole) of 5-acetyl-2-hydroxy-benzamide (1), 30 ml of DMSO and 50 ml n-butanol. While stirring, the resulting slurry is heated to 95° C. To the resulting solution is charged, via the addition funnel, a solution of 4.5 g (0.056 mole) of HBr gas dissolved in 50 ml of n-butanol over 20 minutes. During the addition the reaction temperature is allowed to rise to 98° C. The progress of the reaction is followed by the disappearance of 5-acetyl'2-hydroxy-benzamide (1)(retention time ($t_r$)=2.23 min.) via HPLC (70:30, acetonitrile:water, plus 2.5% acetic acid, 1.5 ml/min, 254 nm, using a Zorbax ODS 4.6 mm×25 cm column). After 20 min. the heat is removed and the reaction mixture containing 5-(dibutyloxyacetyl)-2-hydroxybenzamide (5) and 5-(butyloxyhydroxyacetyl)-2-hydroxybenzamide (6) is quenched with 100 ml ice and stirred for 3 min. The resulting layers are separated and the n-butanol layer is further washed with 100 ml water, followed by the addition of 150 ml water. The n-butanol is azeotroped under vacuum at 32° C. until 200 ml distillate is collected. To the resulting solution is added 50 ml of isopropanol, the suspension is stirred for ten minutes and cooled to 20° C. The resulting slurry is charged with 50 ml of concentrated hydrochloric acid via the addition funnel while controlling the temperature between 20°-25° C. The reaction mixture is then stirred at room temperature. The hydrolysis is considered complete (9.5 hours) by HPLC when less than 0.5% of the 5-(dibutyloxyacetyl)-2-hydroxybenzamide (5) remains ($t_r$=6.7 minutes), at which time 250 ml of water are added over a 30 minute period. The reaction mixture is then cooled to about 5° C., stirred for 20 minutes, filtered, and the filtrate cake is washed with 150 ml water, 50 ml of isopropanol/water (1/1), and finally with 100 ml water. The cake is dried overnight in a draft oven at 45° C. to give 12.6 g of title compound (10), a light yellow solid (85.5% yield).

EXAMPLE 3

5-(Dimethoxyacetyl)-2-hydroxybenzamide (8)

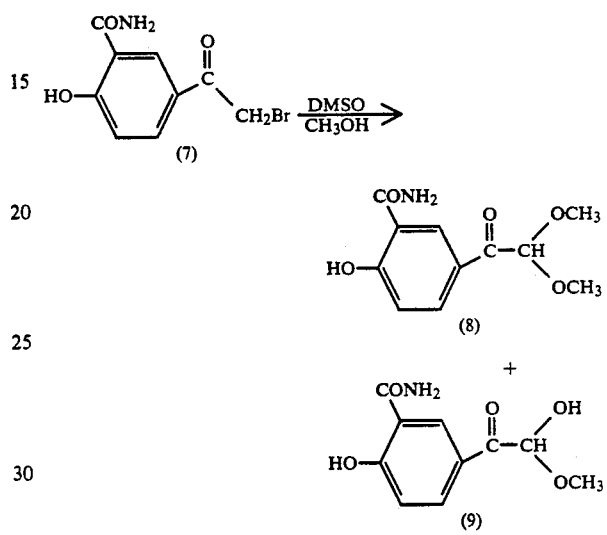

To a 2 L three-necked round-bottomed flask fitted with an overhead mechanical stirrer and a reflux condenser, 180 ml of DMSO are added followed by 100 g (0.388 mole) of 5-(bromoacetyl)-2-hydroxybenzamide (7). The reaction mixture is stirred until a homogeneous solution is obtained. One liter of methanol is added to the reaction mixture and the reaction mixture is heated to reflux in an oil-bath at 85°-90° C. under nitrogen atmosphere. The progress of the reaction is monitored either by HPLC or by $^1$HNMR. When there is no more starting material left (about 22 hr reflux), the reaction is judged to be complete. The reaction mixture contains about 70% 5-(Dimethoxyacetyl)-2-hydroxybenzamide and about 30% 2-hydroxy-5-(hydroxymethoxyacetyl)-benzamide at this stage. Approximately one liter of methanol is distilled off under reduced pressure and the residue is poured onto 1.5 L of ice-water. 5-(Dimethoxyacetyl)-2-hydroxybenzamide precipitates out preferentially, which is filtered, washed with water and dried under vacuum to give 66 g (71% yield) of the title compound (8).

EXAMPLE 4

5-(Dihydroxyacetyl)-2-hydroxybenzamide (10)

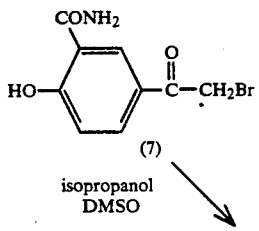

17

-continued

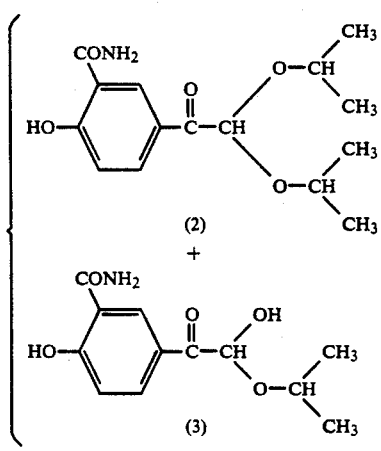

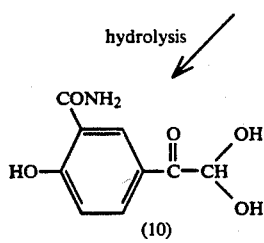

To a 500 ml three-necked round bottomed flask fitted with an overhead mechanical stirrer and reflux condenser, 33 ml of dimethylsulfoxide and 200 ml of sieve-dried isopropanol are added, followed by the addition of 20 g (0.077 mole) of 5-(bromoacetyl)-2-hydroxybenzamide. The reaction mixture is heated to reflux in an oil-bath maintaining the internal temperature of the reaction mixture at 85°–90° C. for 5 hr. Two hundred ml of water are added and the isopropanol is distilled off as an azeotropic mixture (130 ml) at atmospheric pressure. Additional 130 ml of water are added and distillation is continued under reduced pressure until another 70 ml of distillate are collected. The mixture is cooled, pale white crystals are filtered, washed with water and dried overnight in a draft oven at 45° C. to give 15.14 g of title compound (10) (92% yield).

EXAMPLE 5

5-Glyoxyloyl-salicylic acid methyl ester hydrate Using Gaseous HBr

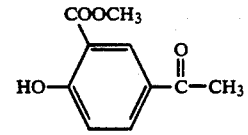

Methyl 5-Acetylsalicylate

DMSO, HBr (gas)
IPA

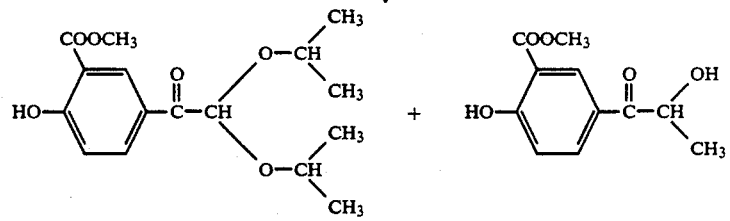

Methyl 5-[bis(1-methyl-ethoxy)acetyl]-2-hydroxybenzoate

Methyl 5-[(hydroxy-1-methylethoxy)acetyl]-2-hydroxybenzoate hydrolysis

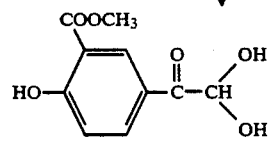

5-Glyoxyloyl-salicylic acid methyl ester hydrate

To a 3-neck flask immersed in an oil bath containing a solution of 40 g (0.206 mole) methyl 5-acetylsalicylate in 60 ml methylene chloride, is charged 70 ml of isopropanol. The solution is distilled to remove excess methylene chloride. When the internal temperature reaches 77° C., 126 ml (1.77 moles) DMSO is added to the mixture and the temperature of the reaction mixture is increased to 80° C. HBr gas (10.85 g, 0.134 moles or 0.65 equivalents) in 40 ml isopropanol is added to the mixture over a period of 20 minutes (exothermic), while the bath is maintained at a temperature of about 85° to 90° C. As one-half of the HBr is added, the mixture is stirred, dimethylsulfide ((CH3)2S) and isopropanol are distilled off and the volume of the distillate is monitored. After distillation of 82 ml of solvent, 20 ml of isopropanol (IPA) is added slowly, while maintaining a steady rate of distillation. After the reaction is complete, as determined by high performance liquid chromatography (HPLC), 81 ml of 2.4N sulfuric acid (H2SO4) is added to the reaction mixture, the reaction temperature is lowered to 75° C. and the residual isopropanol is distilled off under vacuum. A batch temperature of 70°–75° C. is maintained throughout the distillation. After 120 ml total of distillate is collected, the title compound begins to precipitate. Water (70 ml) is added slowly at 75° C. with stirring. After 30 minutes of stirring, the reaction is cooled to 15° C. over a period of 90 minutes to complete the precipitation. The reaction mixture is filtered, the cake is washed with three 60 ml portions of water and dried at 50° C. for 16 hours, to give 39.6 g of the title ketoaldehyde hydrate (85% yield).

EXAMPLE 6

5-Glyoxyloyl-salicylic acid methyl ester hydrate Using Aqueous HBr

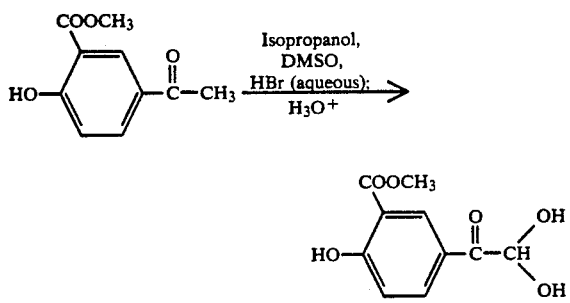

To a 3-neck flask immersed in an oil bath containing a solution of 40 g (0.206 mole) methyl 5-acetylsalicylate in 6 ml methylene chloride is charged with 82 ml of isopropanol. The solution is distilled to remove excess methylene chloride. When the internal temperature reaches 77° C., 126 ml (1.77 mole or 8.6 equivalents) of DMSO is added to the reaction mixture and the temperature of the mixture is increased to a temperature of 85° to 90° C. Then 33 ml (0.29 mole or 1.4 equivalents) or HBr (aqueous, 48%) is added to the mixture over a period of 20 minutes (exothermic), and the bath temperature is maintained at 95° to 100° C. As the addition of HBr nears completion distillation is initiated and dimethylsulfide and isopropanol are distilled off. The mixture is stirred and the volume of the distillate monitored. After distillation of 82 ml of solvent, 20 ml of IPA is added slowly to maintain a steady rate of distillation. After the reaction completed as determined by high performance liquid chromatography (HPLC), the reaction mixture is quenched with 70 ml of 2.4N $H_2SO_4$, the temperature of the reaction mixture is allowed to drop to 75° C. and residual isopropanol is distilled off under vacuum. After a total of 165 ml distillate is collected, the title compound begins to precipitate. A mixture of 30 ml of acetonitrile ($CH_3CN$) and 70 ml of water is added slowly at 75° C. with stirring. After 30 minutes of stirring, the reaction mixture is cooled to 15° C. over a period of 90 minutes to complete the precipitation. The reaction mixture is filtered and the cake is washed with three 300 ml portions of water. The cake is dried in a draft oven at 50° C. for 16 hours to give 39.5 g of the title compound (85% yield).

EXAMPLE 7

Preparation of Albuterol from 5-Glyoxyloyl-salicylic acid methyl ester hydrate

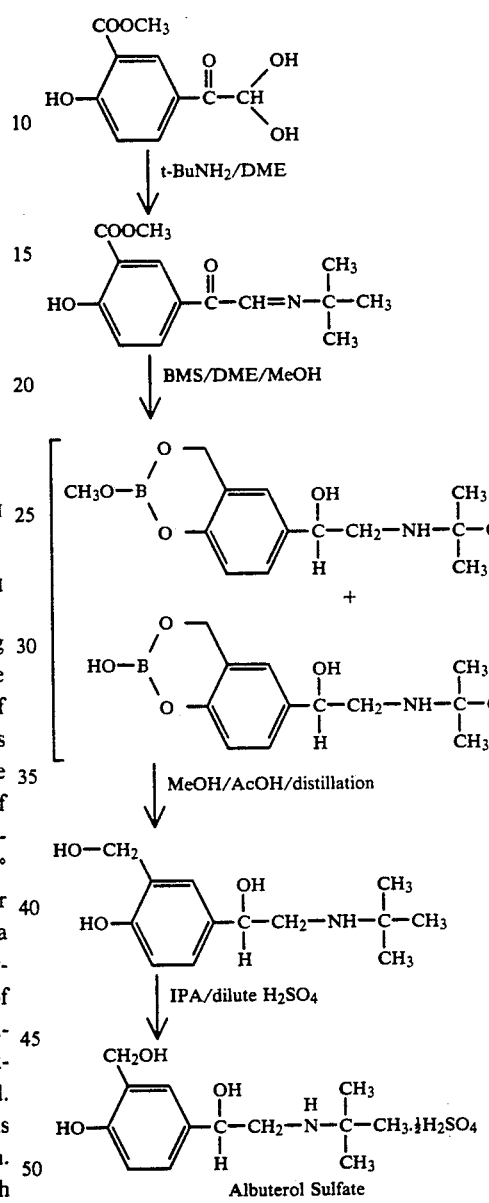

To a solution of 5-glyoxyloylsalicylic acid methyl ester hydrate (50 g, 0.221 mol) in DME (ethylene glycol diethyl ether, 440 mL) is added tertiary butylamine (16.2 g, 0.221 mol) at room temperature. The resulting light orange solution is stirred for 5 min until a clear solution is formed. The clear solution is then heated to reflux. Water and DME are distilled off azeotropically. After a total of 200 ml of distillate are collected, the solution is cooled to 25° C. The reaction mixture is slowly added to a solution containing 49 mL (0.49 mol) of 10.0M borane-dimethyl sulfide (BMS) in 220 mL of DME at 70° C. The resulting reaction mixture is further refluxed for 2.5 hrs. After the reaction is completed as monitored by HPLC, excess DME is removed via vacuum distillation. The residue containing complexes of boron and aryethanolamine is subsequently cooled to 0°

C. Quenching of the residue with 300 mL methanol gives the methylborate of arylethanolamine. The borate is then removed by azeotropic distillation as trimethylborate (B(OCH$_3$)$_3$), leaving behind the desired arylethanolamine in the reaction mixture. An additional 300 ml of methanol and acetic acid (85 mL) are added to ensure the complete removal of trimethylborate via vacuum distillation to near dryness. The residue containing the boron-free aryethanolamine is cooled to 25° C. and concentrated sulfuric acid (10.4 g, 0.221 mole) in water (64 mL) is added following by 570 ml of isopropyl alcohol. Albuterol sulfate is precipitated out as a white solid. After the reaction mixture is stirred at room temperature for 12 hrs and 0° C. for 30 min the albuterol sulfate is filtered, washed with isopropyl alcohol (two 50 mL portions) and dried at 50° C. for 12 hrs to give 49.75 g of the title compound (78% yield).

We claim:

1. The boron-arylethanolamine complex represented in its monomeric form as formulas (XIII)-A and -B:

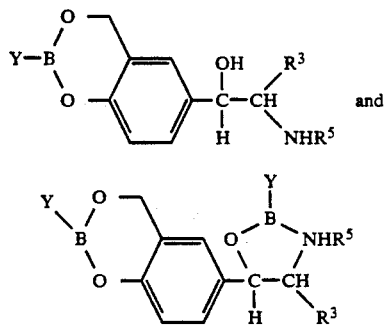

wherein Y is —OR$^{17}$ or —OH, wherein R$^{17}$ is C-1 to C-6 alkyl and R$^3$ and R$^5$ independently represent hydrogen, alkyl, aryl or substituted aryl.

2. A process for preparing an arylethanolamine of the formula:

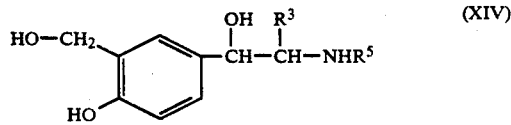

wherein R$^3$ and R$^5$ independently represent hydrogen, alkyl, aryl or substituted aryl, comprising cleaving a boron-arylethanolamine complex of the general formula (XIII)-A or -B of claim 1 to give the desired arylethanolamine (XIV).

3. The process of claim 2 wherein boron-arylethanolamine complex (XIII)-A or -B is cleaved by addition of an acid and an alcohol to the reaction mixture.

4. The process of claim 3 wherein the arylethanolamine (XIV) is recovered by distillation of spent boron out of the reaction mixture.

5. A process for preparing the arylethanolamine of the formula:

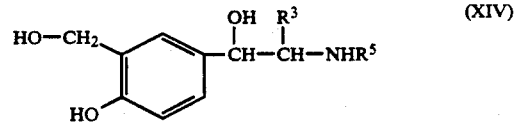

wherein R$^3$ and R$^5$ independently represent hydrogen, alkyl, aryl or substituted aryl, comprising reducing a Schiff's base of the formula:

wherein R$^3$ and R$^5$ are as defined above and Ar' is

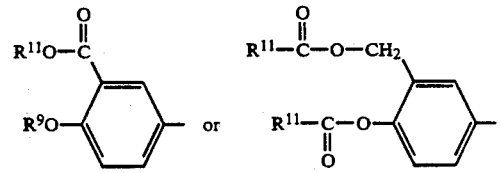

wherein R$^9$ represents hydrogen or acyl, and R$^{11}$ represents hydrogen or alkyl, with a borane-thioether reagent to form a boron-arylethanolamine complex, and cleaving the boron-arylethanolamine complex to give the desired arylethanolamine (XIV).

6. The process of claim 5 wherein the borane-thioether reagent is of the formula:

wherein R$^{13}$ and R$^{15}$, which may be the same or different, represent C-1 to C-6 alkyl, or, together with the sulfur atom, represent a ring containing from 3 to 6 carbon atoms and 1 or 2 sulfur or oxygen atoms, or together with the sulfur atom represent a polymeric thiohydrocarbon.

7. The process of claim 5 characterized in that the Schiff's base (XI) is prepared by condensation of a glyoxal hydrate of formula (IX):

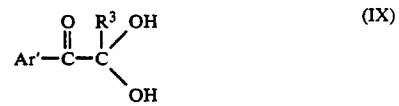

or a hemi-acetal of formula (V):

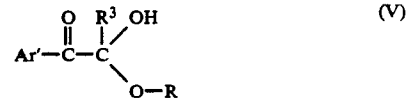

wherein Ar' and R$^3$ are as defined in the claim 5, and R represents alkyl, substituted alkyl, cycloalkyl, cycloalkylalkyl, hydroxyalkyl, aryl, substituted aryl, arylalkyl, substituted arylalkyl, heterocyclic or heterocyclic alkyl, with an amine of the formula H$_2$NR$^5$ (X), wherein R$^5$ represents hydrogen, alkyl or aryl or substituted aryl.

8. The process of claim 7 characterized in that the glyoxal hydrate (IX) is prepared by hydrolyzing an acetal (VII) or hemi-acetal (V)

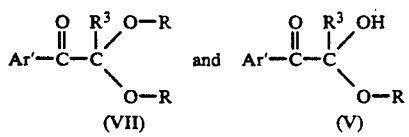

wherein Ar' and $R^3$ are as defined in claim 5 and R represents alkyl, substituted alkyl, cycloalkyl, cycloalkylalkyl, hydroxyalkyl, aryl, substituted aryl, arylalkyl, substituted arylalkyl, heterocyclic or heterocyclic alkyl.

9. The process of claim 8 characterized in that the acetal (VII) or hemi-acetal (V) is prepared by contacting a compound of formula (II):

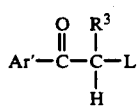

wherein Ar' and $R^3$ are as defined in claim 2 and L is a leaving group, with a sulfoxide and an alcohol of the formula ROH, wherein R is as defined in claim 8, or alternatively, contacting a compound of formula (I):

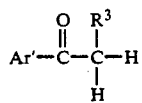

wherein Ar' and $R^3$ are as defined in claim 5, with a halogenating agent, a sulfoxide, and an alcohol of formula ROH as defined above.

10. A process for preparing acetals and hemi-acetals of formulas (VII) or (V):

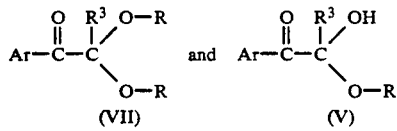

wherein Ar represents aryl or substituted aryl; R represents alkyl, substituted alkyl, cycloalkyl, cycloalkylalkyl, hydroxyalkyl, aryl, substituted aryl, arylalkyl, substituted arylalkyl, heterocyclic or heterocyclic alkyl and $R^3$ represents hydrogen, alkyl, aryl or substituted aryl, comprising contacting a compound of formula (II):

wherein Ar and $R^3$ are as defined above and L is a leaving group, with a sulfoxide and an alcohol of the formula ROH wherein R is as defined above, or alternatively, contacting a compound of formula (I):

wherein Ar and $R^3$ are as defined above, with a halogenating agent, a sulfoxide, and an alcohol of formula ROH wherein R is as defined above, to give the acetal or hemi-acetal of formula (VII) or (V).

11. A process for preparing glyoxal hydrates of formula (IX):

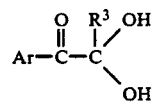

wherein Ar and $R^3$ are as defined in claim 10, comprising hydrolyzing an acetal or hemi-acetal of formulas (VII) and (V), respectively, set forth in claim 10.

12. Acetals and hemi-acetals of the formula:

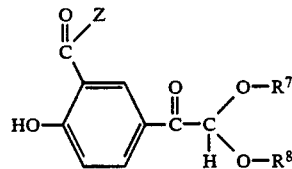

wherein Z is $-NH_2$, $-OH$ or $-OR^6$, where $R^6$ represents hydrogen or alkyl of one to ten carbon atoms, and $R^7$ and $R^8$ independently represent hydrogen, alkyl, substituted alkyl, cycloalkyl, cycloalkylalkyl, hydroxyalkyl, aryl, substituted aryl, arylalkyl, substituted arylalkyl, heterocyclic or heterocyclic alkyl with the proviso that only one of $R^7$ or $R^8$ is hydrogen, or $R^7$ and $R^8$ together with the oxygen atoms forms a five or six membered ring.

13. The acetal or hemi-acetal of claim 12 wherein Z is $-OCH_3$.

14. The acetal or hemi-acetal of claim 13 which is methyl 5-(bis(1-methylethoxy)acetyl)-2-hydroxybenzoate or
methyl 5-((hydroxy-1-methylethoxy)acetyl)-2-hydroxybenzoate.

* * * * *